United States Patent [19]

Yoshida et al.

[11] Patent Number: 5,411,932
[45] Date of Patent: May 2, 1995

[54] HERBICIDAL OIL-BASED SUSPENSION COMPRISING NICOSULFURON AND UREA AS A STABILIZING AGENT

[75] Inventors: Tsunezo Yoshida; Yasuhide Kuriyama; Shigehisa Kanbayashi, all of Kusatsu, Japan

[73] Assignee: Ishihara Sangyo Kaisha Ltd., Osaka, Japan

[21] Appl. No.: 9,984

[22] Filed: Jan. 27, 1993

[30] Foreign Application Priority Data

Jan. 28, 1992 [JP] Japan ................................ 4-053048
May 22, 1992 [JP] Japan ................................ 4-174651

[51] Int. Cl.⁶ .................... A01N 25/22; A01N 43/54; A01N 47/36
[52] U.S. Cl. .................... 504/132; 504/134; 504/136; 504/215; 71/DIG. 1
[58] Field of Search ............... 504/136, 215, 132, 134; 71/DIG. 1; A01N 25/22

[56] References Cited

U.S. PATENT DOCUMENTS

| | | | |
|---|---|---|---|
| 4,659,823 | 4/1987 | Moore, Jr. | 504/215 |
| 5,120,869 | 6/1992 | Cartwright | 504/256 |

FOREIGN PATENT DOCUMENTS

| | | |
|---|---|---|
| 0124295 | 11/1984 | European Pat. Off. |
| 0232067 | 8/1987 | European Pat. Off. |
| 0313317 | 4/1989 | European Pat. Off. |
| 252748 | 12/1987 | Germany |
| 50-40739 | 4/1975 | Japan |
| 51-7128 | 1/1976 | Japan |
| 51-12930 | 1/1976 | Japan |
| 52-117422 | 10/1977 | Japan |
| 57-18605 | 1/1982 | Japan |
| 62-84004 | 4/1987 | Japan |
| 63-23806 | 2/1988 | Japan |
| 2074871 | 11/1981 | United Kingdom |

*Primary Examiner*—S. Mark Clardy
*Attorney, Agent, or Firm*—Sughrue, Mion, Zinn, Macpeak & Seas

[57] ABSTRACT

Disclosed is a chemically stabilized herbicidal oil-based suspension, comprising N-[(4,6-dimethoxypyrimidin-2-yl) aminocarbonyl-3-dimethylaminocarbonyl-2-pyridinesulfonamide (nicosufluron) and/or its salt as an effective herbicidal component, urea, a vegetable oil and/or mineral oil, a surfactant and, as desired, an additional herbicidal component, a thickener, a solvent and other adjuvants. The present invention is characterized in that urea is added to a herbicidal oil-based suspension to suppress decomposition of the effective herbicidal component and to provide a chemically stabilized herbicidal oil-based suspension.

13 Claims, No Drawings

HERBICIDAL OIL-BASED SUSPENSION COMPRISING NICOSULFURON AND UREA AS A STABILIZING AGENT

BACKGROUND OF THE INVENTION

1. Field of the Invention

The present invention relates to a chemically stabilized herbicidal oil-based suspension containing N-[(4,6-dimethoxypyrimidin-2-yl)aminocarbonyl]-3-dimethylaminocarbonyl-2-pyridinesulfonamide (hereinafter referred to as compound A) and/or its salt as an effective herbicidal component, which suppress the decomposition of compound A and/or its salt.

2. Description of the Related Art

The present inventors found previously that pyridinesulfonamide series compounds including compound A and the salts thereof exhibit a very high herbicidal effect when they can be applied to a wide range of weeds including strongly harmful weeds, and filed European Patent Application No. 87300502.9 (or Laid-open European Patent Application No. 232067) on the basis of this finding. The inventors also found that a suspended composition comprising at least one compound selected from the pyridinesulfonamide series compounds and the salts thereof, a vegetable oil and a surfactant, which are mixed at a predetermined ratio, permits improving the herbicidal effect and decreasing the amount of the effective herbicidal component, and filed European Patent Application No. 88309772.7 (or Laid-open European Patent Application No. 313317).

On the other hand, various methods have been proposed to date for suppressing the decomposition of herbicidal sulfonylurea series compounds similar to compound A within preparations of agricultural chemicals so as to stabilize the formulations. For example, a stabilized aqueous composition containing a carboxylate or an inorganic salt is disclosed in Published Unexamined Japanese Patent Application No. 59-205305 (or Laid-open European Patent Application No. 124295). A stabilized granular composition containing calcium carbonate and, as required, sodium tripolyphosphate is disclosed in Published Unexamined Japanese Patent Application No. 62-84004. A stabilized solid formulations of agricultural chemicals containing a mineral-based carrier and a vegetable oil or a solvent having a high boiling point is disclosed in Published Unexamined Japanese Patent Application No. 63-23806. Further, various stabilized compositions of agricultural chemicals containing urea, thiourea or derivatives thereof are disclosed in Published Unexamined Japanese Patent Application No. 50-40739, Published Unexamined Japanese Patent Application No. 51-7128, Published Unexamined Japanese Patent Application No. 51-12930, Published Unexamined Japanese Patent Application No. 52-117422, Published Unexamined Japanese Patent Application No. 56-169606 (or Laid-open Belgian Patent Application No. 888634 or Laid-open British Patent Application No. 2074871), and Published Unexamined Japanese Patent Application No. 57-18605.

However, any of the publications exemplified above does not teach at all an idea of adding urea to a herbicidal oil-based suspension containing compound A and/or a salt thereof for chemically stabilizing it.

SUMMARY OF THE INVENTION

As a result of an extensive research on the measure for chemically stabilizing a herbicidal oil-based suspension containing compound A and/or its salt, the present inventors have found that compound A and/or its salt can be prevented from decomposition by adding urea to the suspension so as to chemically stabilize it, arriving at the present invention.

According to the present invention, there is provided a chemically stabilized herbicidal oil-based suspension, comprising compound A and/or its salt, urea, a vegetable oil and/or mineral oil, and a surfactant.

The present invention also provides a chemically stabilized herbicidal oil-based suspension, comprising compound A and/or its salt, urea, a vegetable oil and/or mineral oil, a surfactant, and at least one additional herbicidal component (hereinafter referred to as other specified herbicidal component(s)) selected from the group consisting of 2,4-dichlorophenoxyacetic acid (common name: 2,4-D), its alkyl ester and salt, 3,6-dichloro-2-methoxybenzoicacid (common name: dicamba) and its salt, 2-chloro-4-ethylamino-6-isopropylamino-s-triazine (common name: atrazine), 3-(1-methylethyl)-1H-2,1,3-benzothiadiazin-4(3H)-one-2,2-dioxide (common name: bentazone), 2-chloro-2',6'-diethyl-N-(methoxymethyl)acetanilide (common name: alachlor), 2-chloro-6'-ethyl-N-(2-methoxy-1-methylethyl)acetootoluidide (common name: metolachlor), 2-chloro-N-isopropylacetanilide (common name: propachlor), N-(1-ethylpropyl)-2,6-dinitro-3,4-xylidine (common name: pendimethalin), 2-(3,5-dichlorophenyl)-2-(2,2,2-trichloroethyl)oxirane (common name: tridiphane), methyl 2-[[[4,6-bis-(difluoromethoxy)-pyrimidin-2-yl]aminocarbonyl]aminosulfonyl]benzoate (common name: primisulfuron-methyl) and its salt, 3,5-dibromo-4-hydroxybenzonitrile (common name: bromoxynil), its carboxylic acid ester and salt, 5,7-dimethyl-N-(2,6-dichlorophenyl)-1,2,4-triazolo [1,5-a]pyrimidine-2-sulfonamide (D489: a compound described in Plant Physiology, 1990, Vol. 93, pages 962 to 966), 2-chloro-N-(ethoxymethyl)-2'-ethyl-6'-methylacetanilide (common name: acetochlor), O-(6-chloro-3-phenyl-4-pyridazinyl) S-octylcarbonothioate (common name: pyridate), 1-(4,6-dimethoxypyrimidin-2-yl)-3-(3-ethylsulfonyl-2-pyridylsulfonyl)urea (DPX-E9636: a compound described in Short Review of Herbicides & PGRs, 1991, page 94) and its salt, 2-[2-chloro-4-(methylsulfonyl)benzoyl]-1,3-cyclohexanedione (common name: sulcotrione) and its salt, methyl 3-chloro-5-(4,6-dimethoxypyrimidin-2-ylcarbamoylsulfamoyl)-1-methylpyrazole-4-carboxylate (NC-319: a compound described in BRIGHTON CROP PROTECTION CONFERENCE-Weeds-1991, page 31) and its salt, and 3-(3,4-dichlorophenyl)-1-methoxy-1-methylurea (common name: linuron).

In other words, in a herbicidal oil-based suspension comprising compound A and/or its salt as an effective herbicidal component, or in a herbicidal oil-based suspension comprising compound A and/or its salt as well as other specified herbicidal component(s) as an effective herbicidal component, the chemically stabilized herbicidal oil-based suspension characterized in that urea is added to said suspension.

DETAILED DESCRIPTION OF THE PREFERRED EMBODIMENTS

The chemically stabilized herbicidal oil-based suspension of the present invention comprises compound A and/or its salt, and, as required, other specified herbicidal component(s), and, urea, a vegetable oil and/or mineral oil, a surfactant and, optionally, a thickener, a solvent and other adjuvants. These components are mixed uniformly, or optional components are mixed in advance, followed by adding the other components, so as to obtain the suspension of the present invention in the form of an oil-based suspension concentrate or a formulation for ultra low volume spraying. In preparing the suspension of the present invention, it is possible to employ wet-grinding, as required.

The salts of compound A contained in the suspension of the present invention include, for example, salts with alkali metals such as sodium and potassium, salts with alkaline earth metals such as magnesium and calcium, and salts with amines such as monomethylamine, dimethylamine and triethylamine. It is possible for compound A to be present together with a salt thereof.

The other specified herbicidal components include, for example, salts, alkyl esters and carboxylic acid esters. The salts include those similar to the salts of compound A described above, salts with amines such as diolamine and trolamine, and dimethylammonium salt. The alkyl esters include the esters with ethyl, butyl, heptyl, octyl, iso-octyl and butoxyethyl groups. Further, the carboxylic acid esters includes the esters with carboxylic acids such as butanoic acid, heptanoic acid and octanoic acid.

Among the additional herbicidal component, preferred are 2,4-D, its alkyl ester and salt, dicamba and its salt, bromoxynil, its carboxylic acid ester and salt, pyridate, DPX-E9636 and its salt, and sulcotrion and its salt.

The vegetable oil and mineral oil used in the suspension of the present invention include, for example, olive oil, kapok oil, castor oil, papaya oil, camellia oil, palm oil, sesame oil, corn oil, rice bran oil, peanut oil, cotton seed oil, soybean oil, rapeseed oil, linseed oil, tung oil, sunflower oil, safflower oil, and liquid paraffin. Particularly, it is desirable to use corn oil and rapeseed oil. These vegetable oils and mineral oils can be used in the form of a mixture, if necessary.

The surfactant used in the present invention includes, for example, salt of alkyl sulfonic acid, salt of alkylbenzene sulfonic acid, salt of lignin sulfonic acid, polyoxyethyleneglycol alkylether, polyoxyethylene lauryl ether, polyoxyethylene alkyl ether, polyoxyethylene alkylaryl ether, polyoxyethylene fatty acid ester, polyoxypropylene fatty acid ester, polyoxyethylene sorbitan fatty acid ester, polyoxyethylene styrylphenyl ether, salt of polycarboxylic acid, salt of dialkylsulfosuccinic acid, salt of aklyldiglycol ether sulfate, salt of polyoxyethylene alkylaryl ether sulfate, salt of polyoxyethylene alkylaryl phosphoric acid ester, polyoxyethylene hydrogenated castor oil, salt of styrylphenyl phosphoric acid, condensate of naphthalenesulfonate with formalin, salt of benzoic acid, fatty acid polyglyceride, glycerin fatty acid ester, sorbitan monooleic acid ester, polyoxyethylene sorbitan monolauric acid ester, and fatty acid alcohol polyglycol ether. These surfactants can be used in the form of a mixture, if necessary.

The thickener which is contained as required in the chemically stabilized herbicidal oil-based suspension of the present invention includes, for example, silica and bentonite-alkylamino complex. Further, the solvent which is contained as required in chemically stabilized herbicidal oil-based suspension of the present invention includes, for example, aliphatic hydrocarbons such as normal paraffins and isoparaffins; aromatic hydrocarbons such as benzene, alkylbenzene, naphthalene, alkylnaphthalene, diphenyl, and phenyl xylyl ethane; heterocyclic compounds such as N-methylpyrrolidone and 1,3-dimethyl-2-imidazolidinone; alcohols; ethers; ketones; and esters.

The specific materials exemplified above as the thickener and solvent used in the present invention can be used in the form of a mixture, if necessary.

Concerning the mixing ratio of the components, the chemically stabilized herbicidal oil-based suspension of the present invention comprises, based on the total weight of the suspension, 0.5 to 20 parts by weight, preferably 1 to 6 parts by weight, more preferably 2 to 6 parts by weight, of compound A and/or its salt, 0.5 to 75 parts by weight, preferably 0.5 to 50 parts by weight of other specified herbicidal component(s) in the case where the suspension contains said another specified herbicidal component, 0.2 to 10 parts by weight, preferably 0.5 to 5 parts by weight, of urea, 19 to 93.8 parts by weight, preferably 30 to 88 parts by weight, more preferably 38.5 to 88 parts by weight of a vegetable oil and/or mineral oil, 5 to 25 parts by weight, preferably 8 to 15 parts by weight, of a surfactant, 0 to 5 parts by weight, preferably 0.5 to 3 parts by weight, more preferably 1 to 2 parts by weight, of a thickener when added to the suspension, and 0 to 74.8 parts by weight, preferably 10 to 49.5 parts by weight, of a solvent when added to the suspension. Further, suitable amounts of other adjuvants are also contained as required in the suspension of the present invention.

Exemplified below are formulations of the chemically stabilized herbicidal oil-based suspension of the present invention. Of course, the present invention is not restricted to the formulations exemplified below.

FORMULATION EXAMPLE 1

| | Parts by weight |
|---|---|
| (1) Compound A (purity: 93.8%) | 4.91 |
| (2) A mixture of polyoxyethylene nonylphenyl ether, dialkylsulfosuccinate, polyoxyethylene hydrogenated castor oil, and polyglycerol esters of fatty acid (trade name: Sorpol 3815K, manufactured by Toho Chemical Industry, Co., Ltd.) | 12.55 |
| (3) Bentonite-alkylamino complex (trade name: New D ORBEN, manufactured by Shiraishi Kogyo Kaisha, Ltd.) | 2.09 |
| (4) Urea | 1.05 |
| (5) Corn oil | 79.40 |

A mixture of components (1) to (5) was subjected to wet-grinding for 15 minutes using a wet-grinding machine DYNO-MILL type KDL manufactured by Willy A. Bachofen. The wet-grinding machine was loaded at a loading rate of 60% with glass beads having a diameter of 1.0 mm and rotated at a peripheral speed of 10.5 m/sec and an oil-based suspension concentrate was obtained.

FORMULATION EXAMPLE 2

An oil-based suspension concentrate was obtained as in Formulation Example 1, except that urea was used in an amount of 2.09 parts by weight in contrast to 1.05 parts by weight in Formulation Example 1, and that corn oil was used in an amount of 78.36 parts by weight in place of 79.40 parts by weight in Formulation Example 1.

FORMULATION EXAMPLE 3

An oil-based suspension concentrate was obtained as in Formulation Example 1, except that urea was used in an amount of 3.14 parts by weight in contrast to 1.05 parts by weight in Formulation Example 1, and that corn oil was used in an amount of 77.31 parts by weight in place of 79.40 parts by weight in Formulation Example 1.

FORMULATION EXAMPLE 4

An oil-based suspension concentrate was obtained as in Formulation Example 1, except that the wet-grinding was performed for 30 minutes in place of 15 minutes in Formulation Example 1.

FORMULATION EXAMPLE 5

| | Parts by weight |
|---|---|
| (1) Compound A (purity: 93.8%) | 2.79 |
| (2) Octanoic acid ester of 3,5-dibromo-4-hydroxybenzonitrile (purity: 94.6%) | 25.38 |
| (3) A mixture of glycerine fatty acid ester and polyoxyethylene alkylaryl ether (trade name: GERONOL VO/278, manufactured by Rhone-Poulenc) | 9.44 |
| (4) Fine amorphous silica (trade name: AEROSIL R974, manufactured by Degussa) | 0.94 |
| (5) Urea | 0.57 |
| (6) Corn oil | 60.88 |

A mixture of components (1) to (6) was subjected to wet-grinding for 15 minutes with the same wet-grinding machine and conditions as in Formulation Example 1, and an oil-based suspension concentrate was obtained.

FORMULATION EXAMPLE 6

An oil-based suspension concentrate was obtained as in Formulation Example 5, except that urea was used in an amount of 0.75 part by weight in place of 0.57 part by weight in Formulation Example 5, and that corn oil was used in an amount of 60.70 parts by weight in place of 60.88 parts by weight in formulation Example 5.

FORMULATION EXAMPLE 7

An oil-based suspension concentrate was obtained as in Formulation Example 5, except that urea was used in an amount of 0.94 part by weight in place of 0.57 part by weight in Formulation Example 5, and that corn oil was used in an amount of 60.51 parts by weight in place of 60.88 parts by weight in Formulation Example 5.

FORMULATION EXAMPLE 8

An oil-based suspension concentrate was obtained as in Formulation Example 5, except that urea was used in an amount of 1.42 parts by weight in place of 0.57 part by weight in Formulation Example 5, and that corn oil was used in an amount of 60.03 parts by weight in place of 60.88 parts by weight in Formulation Example 5.

FORMULATION EXAMPLE 9

| | Parts by weight |
|---|---|
| (1) Compound A (purity: 93.8%) | 2.79 |
| (2) Octanoic acid ester of 3,5-dibromo-4-hydroxybenzonitrile (purity: 94.6%) | 25.38 |
| (3) GERONOL VO/278 (trade name) | 9.44 |
| (4) AEROSIL R974 (trade name) | 1.51 |
| (5) Urea | 0.94 |
| (6) Aromatic solvent with a high boiling point (trade name: SOLVESSO 200, manufactured by Exxon Chemical Ltd.) | 18.87 |
| (7) Corn oil | 41.07 |

A mixture of components (1) to (7) was subjected to wet-grinding for 15 minutes with the same wet-grinding machine and conditions as in Formulation Example 1, and an oil-based suspension concentrate was obtained.

FORMULATION EXAMPLE 10

An oil-based suspension concentrate was obtained as in Formulation Example 9, except that an aromatic solvent with a high boiling point (trade name: HISOL SAS-296, manufactured by Nippon Petrochemicals Co., Ltd.) was used in place of SOLVESSO 200 (trade name) used in Formulation Example 9.

FORMULATION EXAMPLE 11

An oil-based suspension concentrate was obtained as in Formulation Example 9, except that wet-grinding was performed for 30 minutes in place of 15 minutes in Formulation Example 9.

FORMULATION EXAMPLE 12

| | Parts by weight |
|---|---|
| (1) Compound A (purity: 93.8%) | 4.69 |
| (2) Ethyl 2,4-dichlorophenoxyacetate (purity: 97.8%) | 21.47 |
| (3) GERONOL VO/278 (trade name) | 10.00 |
| (4) AEROSIL R974 (trade name) | 1.00 |
| (5) Urea | 1.00 |
| (6) Corn oil | 61.84 |

A mixture of components (1) to (6) was subjected to wet-grinding for 15 minutes with the same wet-grinding machine and conditions as in Formulation Example 1, and an oil-based suspension concentrate was obtained.

FORMULATION EXAMPLE 13

An oil-based suspension concentrate was obtained as in Formulation Example 12, except that urea was used in an amount of 2.00 parts by weight in place of 1.00 part by weight used in Formulation Example 12, and that corn oil was used in an amount of 60.84 parts by weight in place of 61.84 parts by weight used in Formulation Example 12.

FORMULATION EXAMPLE 14

An oil-based suspension concentrate is obtained as in Formulation Example 1, except that rapeseed oil is used in place of corn oil used in Formulation Example 1.

FORMULATION EXAMPLE 15

An oil-based suspension concentrate is obtained as in Formulation Example 1, except that fatty alcohol polyglycol ether (trade name: Emulsogen EL-100, manufactured by Hoechst) is used in place of Sorpol 3815K (trade name) used in Formulation Example 1.

FORMULATION EXAMPLE 16

| | Parts by weight |
|---|---|
| (1) Compound A (purity: 93.8%) | 2.80 |
| (2) Octanoic acid ester of 3,5-dibromo-4-hydroxybenzonitrile (purity: 94.2%) | 25.49 |
| (3) GERONOL VO/278 (trade name) | 11.32 |
| (4) Bentonite-alkylamino complex (trade name: BENTONE SD-l, manufactured by RHEOX, Inc.) | 2.36 |
| (5) HISOL SAS-296 (trade name) | 18.87 |
| (6) Urea | 0.94 |
| (7) Rapeseed oil | 38.22 |

A mixture of components (1) to (7) was subjected to wet-grinding for 15 minutes with the same wet-grinding machine and conditions as in Formulation Example 1, and an oil-based suspension concentrate was obtained.

FORMULATION EXAMPLE 17

| | Parts by weight |
|---|---|
| (1) Compound A (purity: 93.8%) | 2.45 |
| (2) Sorpol 3815K (trade name) | 12.55 |
| (3) New D ORBEN (trade name) | 2.09 |
| (4) Urea | 1.05 |
| (5) Corn oil | 81.86 |

A mixture of components (1) to (5) is subjected to wet-grinding for 15 minutes with the same wet-grinding machine and conditions as in Formulation Example 1, and a formulation for ultra low volume spraying is obtained.

FORMULATION EXAMPLE 18

A formulation for ultra low volume spraying is obtained as in Formulation Example 17, except that compound A is used in an amount of 1.23 parts by weight in place of 2.45 parts by weight used in Formulation Example 17, and that corn oil is used in an amount of 83.08 parts by weight in place of 81.86 parts by weight used in Formulation Example 17.

FORMULATION EXAMPLE 19

| | Parts by weight |
|---|---|
| (1) Compound A (purity: 93.8%) | 1.40 |
| (2) Octanoic acid ester of 3,5-dibromo-4-hydroxybenzonitrile (purity: 94.6%) | 12.69 |
| (3) GERONOL VO/278 (trade name) | 9.44 |
| (4) AEROSIL R974 (trade name) | 1.51 |
| (5) Urea | 0.94 |
| (6) SOLVESSO 200 (trade name) | 18.87 |
| (7) Corn oil | 55.15 |

A mixture of components (1) to (7) is subjected to wet-grinding for 15 minutes with the same wet-grinding machine and conditions as in Formulation Example 1, and a formulation for ultra low volume spraying is obtained.

COMPARATIVE FORMULATION EXAMPLE 1

| | Parts by weight |
|---|---|
| (1) Compound A (purity: 93.8%) | 4.91 |
| (2) Sorpol 3815K (trade name) | 12.55 |
| (3) New D ORBEN (trade name) | 2.09 |
| (4) Corn oil | 80.45 |

A mixture of components (1) to (4) was subjected to wet-grinding for 15 minutes with the same wet-grinding machine and conditions as in Formulation Example 1, and an oil-based suspension concentrate was obtained.

COMPARATIVE FORMULATION EXAMPLE 2

| | Parts by weight |
|---|---|
| (1) Compound A (purity: 93.8%) | 2.79 |
| (2) Octanoic acid ester of 3,5-dibromo-4-hydroxybenzonitrile (purity: 94.6%) | 25.38 |
| (3) GERONOL VO/278 (trade name) | 9.44 |
| (4) AEROSIL R974 (trade name) | 0.94 |
| (5) Corn oil | 61.45 |

A mixture of components (1) to (5) was subjected to wet-grinding for 15 minutes with the same wet-grinding machine and conditions as in Formulation Example 1, and an oil-based suspension concentrate was obtained.

Comparative Formulation Example 3

| | Parts by weight |
|---|---|
| (1) Compound A (purity: 93.8%) | 4.69 |
| (2) Ethyl 2,4-dichlorophenoxyacetate (purity: 97.8%) | 21.47 |
| (3) GERONOL VO/278 (trade name) | 10.00 |
| (4) AEROSIL R974 (trade name) | 1.00 |
| (5) Corn oil | 62.84 |

A mixture of components (1) to (5) was subjected to wet-grinding for 15 minutes with the same wet-grinding machine and conditions as in Formulation Example 1, and an oil-based suspension concentrate was obtained.

These formulations and comparative formulations were subjected to various tests as follows:

Test 1

50 ml of the oil-based suspension concentrate obtained in each of Formulation Examples 1 to 3 and Comparative Formulation Example 1 was put in a glass container provided with stopper, and subjected to an accelerated storage stability test for one week under a constant temperature of 60° C. The rates of decomposition of compound A were determined with HPLC. The results are shown in Table 1.

TABLE 1

| Formulation Example | Decomposition rate (%) of Compound A |
|---|---|
| 1 | 5.9 |
| 2 | 5.6 |
| 3 | 6.5 |
| Comparative Formulation Example 1 | 12.6 |

As apparent from Table 1, the decomposition of compound A was markedly suppressed in each of Formulation Examples 1 to 3, compared with Comparative Formulation Example 1.

Test 2

50 ml of the oil-based suspension concentrate obtained in each of Formulation Examples 5 to 8 and Comparative Formulation Example 2 was put in a glass container provided with stopper, and subjected to an accelerated storage stability test for one month under a constant temperature of 50° C. and for 2 weeks under a constant temperature of 60° C., respectively. The rates of decomposition of compound A were determined with HPLC after predetermined period. The results are shown in Table 2.

TABLE 2

| Formulation Example | Decomposition rate (%) of Compound A | | | |
|---|---|---|---|---|
| | 50° C. | | 60° C. | |
| | 2 weeks later | 1 month later | 1 week later | 2 weeks later |
| 5 | 1.2 | 2.4 | 4.0 | 5.6 |
| 6 | 1.5 | 2.7 | 3.8 | 4.8 |
| 7 | 0.5 | 1.9 | 3.5 | 3.4 |
| 8 | 0.5 | 2.7 | 0 | 3.4 |
| Comparative Formulation Example 2 | 2.7 | 7.3 | 11.0 | 21.0 |

Table 2 clearly shows that the decomposition of compound A was markedly suppressed in each of Formulation Examples 5 to 8, compared with Comparative Formulation Example 2. Further, decomposition of octanoic acid ester of 3,5-dibromo-4-hydroxybenzonitrile was not recognized in each of these Formulation Examples and Comparative Formulation Example.

Test 3

50 ml of the oil-based suspension concentrate obtained in each of Formulation Examples 9 and 10 was put in a glass container provided with stopper, and subjected to an accelerated storage stability test for one week under a constant temperature of 60° C. The rates of decomposition of compound A were determined with HPLC. The result are shown in Table 3.

TABLE 3

| Formulation Example | Decomposition rate (%) of Compound A |
|---|---|
| 9 | 0 |
| 10 | 0.7 |

Table 3 shows that the decomposition of compound A was markedly suppressed in each of Formulation Examples 9 and 10, as in tests 1 and 2. Further, decomposition of octanoic acid ester of 3,5-dibromo-4-hydroxybenzonitrile was not recognized in each of these Formulation Examples.

Test 4

50 ml of the oil-based suspension concentrate obtained in each of Formulation Examples 12 and 13 and Comparative Formulation Example 3 was put in a glass container provided with stopper, and subjected to an accelerated storage stability test for one month under a constant temperature of 50° C. and for one week under a constant temperature of 60° C., respectively. The rates of decomposition of compound A were determined with HPLC after predetermined period. The results are shown in Table 4.

TABLE 4

| Formulation Example | Decomposition rate (%) of Compound A | | |
|---|---|---|---|
| | 50° C. | | 60° C. |
| | 2 weeks later | 1 month later | 1 week later |
| 12 | 3.8 | 5.4 | 2.7 |
| 13 | 1.6 | 2.1 | 0 |
| Comparative Formulation Example 3 | 2.9 | 7.0 | 12.0 |

Table 4 clearly shows that the decomposition of compound A was markedly suppressed in each of Formulation Examples 12 and 13, compared with Comparative Formulation Example 3. Further, decomposition of ethyl 2,4-dichlorophenoxyacetate was not recognized in each of these Formulation Examples and Comparative Formulation Example.

What is claimed is:

1. A chemically stabilized herbicidal oil-based suspension, comprising N-[(4,6-dimethoxypyrimidin-2-yl)amino-carbonyl]-3-dimethylaminocarbonyl-2-pyridinesulfonamide and/or its salt, urea in an amount of 0.2 to 10 parts by weight for stabilizing the pyridinesulfonamide and/or its salt, a vegetable oil and/or mineral oil, and a surfactant.

2. In an herbicidal oil-based suspension comprising N-[(4,6-dimethoxypyrimidin-2-yl)aminocarbonyl]-3-dimethylaminocarbonyl-2-pyridinesulfonamide and/or its salt as an effective component, a chemically stabilized herbicidal oil-based suspension characterized in that urea is added to said suspension in an amount of 0.2 to 10 parts by weight for stabilizing the pyridinesulfonamide and/or its salt.

3. The chemically stabilized herbicidal oil-based suspension according to claim 1 or 2, wherein said N-[(4,6-dimethoxypyrimidin-2-yl)aminocarbonyl]-3-dimethylaminocarbonyl-2-pyridinesulfonamide and/or its salt is N-[(4,6-dimethoxypyrimidin-2-yl) aminocarbonyl]-3-dimethylaminocarbonyl-2-pyridinesulfonamide.

4. The chemically stabilized herbicidal oil-based suspension according to claim 1, comprising 0.5 to 20 parts by weight of N-[(4,6-dimethoxypyrimidin-2-yl) aminocarbonyl]-3-dimethylaminocarbonyl-2-pyridinesulfonamide and/or its salt, 19 to 93.8 parts by weight of a vegetable oil and/or mineral oil, and 5 to 25 parts by weight of a surfactant.

5. The chemically stabilized herbicidal oil-based suspension according to claim 1, further comprising a thickener and/or a solvent.

6. The chemically stabilized herbicidal oil-based suspension according to claim 1, wherein said vegetable oil and/or mineral oil is a vegetable oil.

7. The chemically stabilized herbicidal oil-based suspension according to claim 6, wherein said vegetable oil is at least one vegetable oil selected from the group consisting of corn oil and rapeseed oil.

8. A chemically stabilized herbicidal oil-based suspension comprising N-[(4,6-dimethoxypyrimidin-2-yl)amino-carbonyl]-3-dimethylaminocarbonyl-2-pyridinesulfonamide and/or its salt, at least one additional herbicidal component, urea in an amount of 0.2 to 10 parts by weight for stabilizing the pyridinesulfonamide and/or its salt, a vegetable and/or mineral oil, and a surfactant, said additional herbicidal component being selected from the group consisting of 2,4-dichlorophenoxyacetic acid, its alkyl ester and salt, 3,6-dichloro-2-methoxybenzoic acid and its salt, 2-chloro-4-ethylamino-6-isopropylamino-s-triazine, 3-(1 methylethyl)-1H-2,1,3-benzothiadiazin-4(3H)-one-2,2-dioxide, 2-chloro-2',6'-diethyl-N-(methoxymethyl)acetanilide, 2-chloro-6'-ethyl-N-(2-methoxy-1-methylethyl)aceto-o-toluidide, 2-chloro-N-isopropylacetanilide, N-(1-ethylpropyl)-2,6-dinitro-3,4-xylidine, 2-(3,5-dichlorophenyl)-2-(2,2,2-trichloroethyl) oxirane, methyl 2-[[[4,6-bis-(difluoromethoxy)-pyrimidin-2-yl]amino-carbonyl]aminosulfonyl]benzoate and its salt, 3,5-dibromo-4-hydroxybenzonitrile, its carboxylic acid ester and salt, 5,7-dimethyl-N-(2,6-dichlorophenyl)-1,2,4-triazolo [1,5-a] pyrimidine-2-sulfonamide, 2-chloro-N-(ethoxymethyl)-2'-ethyl-6'-methylacetanilide, O-(6-chloro-3-phenyl-4-pyridazinyl) S-octylcarbonothioate, 1-(4,6-dimethoxypyrimidin-2-yl)-3-(3-ethylsulfonyl-2-pyridylsulfonyl)urea and its salt, 2-[2-chloro-4-(methylsulfonyl)-benzoyl]-1,3-cyclohexanedione and its salt, methyl 3-chloro-5-(4,6-dimethoxypyrimidin-2-yl)-carbamoylsulfamoyl)-1-methylpyrazole-4-carboxylate and its salt, and 3-(3,4-dichlorophenyl)-1-methoxy-1-methylurea.

9. In a herbicidal oil-based suspension comprising N-[(4,6-dimethoxypyrimidin-2-yl)aminocarbonyl]-3-dimethylaminocarbonyl-2-pyridinesulfonamide and/or its salt and at least one additional herbicidal component selected from the group consisting of 2,4-dichlorophenoxyacetic acid, its alkyl ester and salt, 3,6-dichloro-2-methoxybenzoic acid and its salt, 2-chloro-4-ethylamino-6-isopropylamino-s-triazine, 3-(1-methylethyl)-1H-2,1,3-benzothiadiazin-4(3H)-one-2,2-dioxide, 2-chloro-2',6'-diethyl-N-(methoxymethyl)acetanilide, 2-chloro-6'-ethyl-N-(2-methoxy-1-methylethyl)aceto-o-toluidide, 2-chloro-N-isopropylacetanilide, N-(1-ethylpropyl)-2,6-dinitro-3,4-xylidine, 2-(3,5-dichlorophenyl)-2-(2,2,2-trichloroethyl)oxirane, methyl 2-[[[4,6-bis-(difluoromethoxy)-pyrimidin-2-yl]aminocarbonyl]aminosulfonyl]benzoate and its salt, 3,5-dibromo-4-hydroxybenzonitrile, its carboxylic acid ester and salt, 5,7-dimethyl-N-(2,6-dichlorophenyl)-1,2,4-triazolo[1,5-a]pyrimidine-2-sulfonamide, 2-chloro-N-(ethoxymethyl)-2'-ethyl-6'-methylacetanilide, O-(6-chloro-3-phenyl-4-pyridazinyl) S-octylcarbonothioate, 1-(4,6-dimethoxypyrimidin-2-yl)-3-(3-ethylsulfonyl-2-pyridylsulfonyl) urea and its salt, 2-[2-chloro-4(methylsulfonyl)benzoyl]-1,3-cyclohexanedione and its salt, methyl 3-chloro-5-(4,6-dimethoxypyrimidin-2-yl-carbamoylsulfamoyl)-1-methylpyrazole-4-carboxylate and its salt, and 3-(3,4-dichlorophenyl)-1-methoxy-1-methylurea which are effective components, a chemically stabilized herbicidal oil-based suspension characterized in that urea in an amount of 0.2 to 10 parts by weight for stabilizing the pyridinesulfonamide and/or its salt is added to said suspension.

10. The chemically stabilized herbicidal oil-based suspension according to claim 8, comprising 0.5 to 20 parts by weight of N-[(4,6-dimethoxypyrimidin-2-yl) aminocarbonyl]-3-dimethylaminocarbonyl-2-pyridinesulfonamide and/or its salt, 0.5 to 75 parts by weight of at least one additional herbicidal component, 19 to 93.8 parts by weight of a vegetable oil and/or mineral oil, and 5 to 25 parts by weight of a surfactant.

11. The chemically stabilized herbicidal oil-based suspension according to claim 8 or 9, wherein said additional herbicidal component is selected from the group consisting of 2,4-dichlorophenoxyacetic acid, its alkyl ester and salt, 3,6-dichloro-2-methoxybenzoic acid and its salt, 3,5-dibromo-4-hydroxybenzonitrile, its carboxylic acid ester and salt,
O-(6-chloro-3-phenyl-4-pyridazinyl) S-octylcarbonothioate,
1-(4,6-dimethoxypyrimidin-2-yl)-3-(3-ethylsulfonyl-2-pyridylsulfonyl) urea and its salt, and
2-[2-chloro-4-(methylsulfonyl) benzoyl]-1,3-cyclohexanedione and its salt.

12. The chemically stabilized herbicidal oil-based suspension according to claim 8 or 9, wherein said additional herbicidal component is selected from the group consisting of 2,4-dichlorophenoxyacetic acid, its alkyl ester and salt, and 3,5-dibromo-4-hydroxybenzonitrile, its carboxylic acid ester and salt.

13. A method of suppressing decomposition of N-[(4,6-dimethoxypyrimidin-2-yl)aminocarbonyl]-3-dimethylaminocarbonyl-2-pyridinesulfonamide and/or its salt contained as a component in an oil-based suspension which comprises providing urea in an amount for suppressing decomposition of said pyridinesulfonamide and/or its salt to the oil-based suspension.

* * * * *